United States Patent [19]

Hilpert

[11] Patent Number: 5,698,698
[45] Date of Patent: Dec. 16, 1997

[54] PROCESS FOR PREPARATION OF N-TERT.BUTYL-DECAHYDRO-2-[2(R)-HYDROXY-4-PHENYL-3(S)-PHTHALIMIDOBUTYL]-(4AS,8AS)-ISOQUINOLINE-3(S)-CARBOXAMIDE

[75] Inventor: Hans Hilpert, Reinach, Switzerland

[73] Assignee: Hoffmann-La Roche Inc., Nutley, N.J.

[21] Appl. No.: 814,389

[22] Filed: Mar. 11, 1997

Related U.S. Application Data

[62] Division of Ser. No. 575,193, Dec. 20, 1995, Pat. No. 5,641,886, which is a division of Ser. No. 273,088, Jul. 11, 1994, Pat. No. 5,502,210.

[30] Foreign Application Priority Data

Jul. 15, 1993 [CH] Switzerland ............... 2132/93
Aug. 4, 1993 [CH] Switzerland ............... 2330/93

[51] Int. Cl.$^6$ ................................. C07D 401/02
[52] U.S. Cl. ................................. 546/146
[58] Field of Search ........................ 546/146

[56] References Cited

U.S. PATENT DOCUMENTS

| | | |
|---|---|---|
| 5,196,438 | 3/1993 | Martin et al. ............ 546/146 |
| 5,451,678 | 9/1995 | Parkes et al. ............ 546/146 |

FOREIGN PATENT DOCUMENTS

| | | |
|---|---|---|
| 2030415 | 6/1991 | Canada . |
| 0432694 | 12/1990 | European Pat. Off. . |
| 408340 | 1/1991 | European Pat. Off. . |
| 93/15091 | 8/1993 | WIPO . |

OTHER PUBLICATIONS

Hassal et al., Heterocycles 7:119–122 (1977).
Hassall et al., J. Chem. Soc. Perkin Transactions I, pp. 155–166 (1984).
Ikarya et al., J. Chem. Soc. Chem. Commun. pp. 922–924 (1985).
Parkes, et al., J. Org. Chem. vol. 59 (1994) pp. 3656–3664.
Sasai et al., Tetrahedron Letters vol. 35, No. 33 1994 pp. 6123–6126.
Gao et al., J. of the American Chem. Society 110, 1988, 7538–7539.
Lohray et al., Tetrahedron Lett. 30(20) 1989, 2623–2626.
Chem. Abstracts 114(21), 1991, Abstr. No. 206159q and J. Chemical Society 2, 1991, 95–97, Lohray et al.
Patent Abstr. of Japan, 011 (069), (C–407) 1987 & JP A–61 227578.

*Primary Examiner*—Zinna Northington Davis
*Attorney, Agent, or Firm*—George W. Johnston; Ellen Ciambrone Coletti; Robert A. Silverman

[57] ABSTRACT

The invention relates to a process for the preparation of N-tert.butyl-decahydro-2-[2(R)-hydroxy-4-phenyl-3(S)-phthalimidobutyl]-(4aS,8aS)-isoquinoline-3(S)-carboxamide of the formula

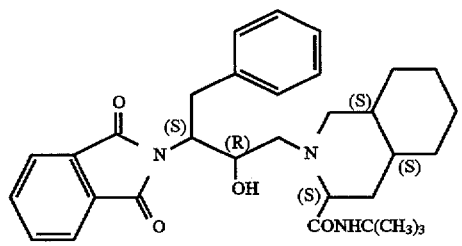

I as well as novel intermediates. The compound of formula I, specifically described in Example 1 of European Patent Publication 0,432,694, is a valuable intermediate for pharmacologically active compounds. The compound of formula I can be converted into pharmacologically active compounds which are suitable for the treatment of viral infections, such as those caused by HIV and other retroviruses.

2 Claims, No Drawings

PROCESS FOR PREPARATION OF N-TERT.BUTYL-DECAHYDRO-2-[2(R)-HYDROXY-4-PHENYL-3(S)-PHTHALIMIDOBUTYL]-(4AS,8AS)-ISOQUINOLINE-3(S)-CARBOXAMIDE

This is a continuation of application Ser. No. 08/575,193, filed Dec. 20, 1995 now U.S. Pat. No. 5,641,886, which is a Rule 60 Divisional of Ser. No. 08/273,088, filed Jul. 11, 1994 now U.S. Pat. No. 5,502,210.

BRIEF SUMMARY OF THE INVENTION

The invention relates to a process for the preparation of N-tert.butyl-decahydro-2-[2(R)-hydroxy-4-phenyl-3(S)-phthalimidobutyl]-(4aS,8aS)-isoquinoline-3(S)-carboxamide of the formula

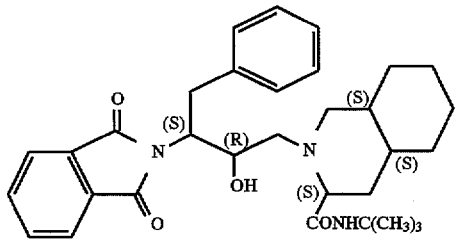

I as well as intermediates.

The compound of formula I, specifically described in Example 1 of European Patent Publication 0,432,694, is a valuable intermediate for pharmacologically active compounds. The compound of formula I can be converted into pharmacologically active compounds which are suitable for the treatment of viral infections, such as those caused by HIV and other retroviruses.

DETAILED DESCRIPTION OF THE INVENTION

The process in accordance with the invention comprises a) reductively aminating (2S,3S)-3-(1,3-dioxo-2,3-dihydro-1H-isoindol-2-yl)-2-hydroxy-4-phenylbutyraldehyde of the formula

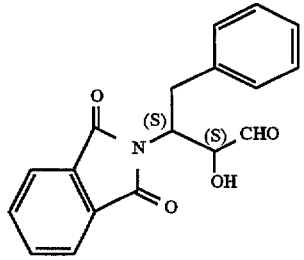

II with N-tert.butyl-decahydro-(4aS,8aS)-isoquinoline-3(S)-carboxamide of the formula

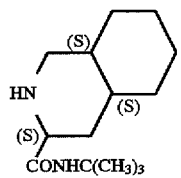

III b) reacting a 1,3,2-dioxathiolane derivative of the formula

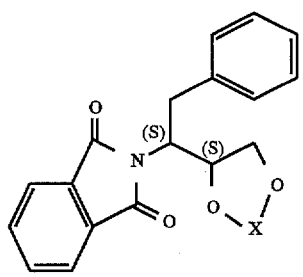

IV wherein X is SO or $S_{O2}$, with the compound of formula III.

The reductive amination of the hydroxyaldehyde of formula II with the compound of formula III is effected in a known manner. Thus, it can be carried out in a solvent such as methanol in the presence of an alkali metal borohydride, for example, an alkali metal cyanoborohydride of the formula $MBH_3CN$, wherein M is an alkali metal such as lithium or sodium, and an acid such as hydrochloric acid. In a variant, a solution of the compounds of formulas II and III in an acid such as acetic acid is treated with lithium cyanoborohydride or sodium cyanoborohydride. In a further variant, a solution of the compounds of formulas II and III in formic acid is heated to reflux.

The reaction of a compound of formula IV above with the compound of formula III above is also carried out in a known manner, depending on the significance of X in formula IV. Thus, the compound of formula IV in which X is SO can be reacted with the compound of formula III according to the method of B. B. Lohray and J. R. Ahuja [J. Chem. Soc., Chem. Commun. 1991, 95] in the presence of a base such as an alkylamine, for example triethylamine, or an alkali carbonate, for example potassium or sodium carbonate, and the like in a high-boiling organic solvent which is inert under the reaction conditions, such as isobutyl methyl ketone and the like, at a temperature of about 50°–150° C., preferably at about 110° C. The compound of formula IV in which X is $SO_2$ can be reacted according to the method of Y. Gao and K. B. Sharpless [JACS 110, 7538 (1988)] in an organic solvent which is inert under the reaction conditions, such as an ether, for example diethyl ether, tetrahydrofuran or dioxane, and the like at a temperature between about 0° and 80°, preferably at room temperature, with the compound of formula III, and then hydrolyzed in the presence of a strong aqueous acid such as a mineral acid, for example sulphuric acid and the like.

The compound of formula III is the compound of formula VII in European Patent Publication 0,432,695.

The invention also relates to the compounds of formulas II and IV. They can be prepared as described in the following Reaction Schemes. In the following Reaction Schemes, R is lower alkyl or phenyl, which can be substituted by one or two halogen atoms.

The term "lower-alkyl" denotes straight-chain and branched saturated hydrocarbon residues with 1–6, preferably 1–4, carbon atoms such as methyl, ethyl, n-propyl, isopropyl, n-butyl, isobutyl, sec.butyl tert.butyl, pentyl, hexyl and the like. The term "halogen" denotes fluorine, chlorine, bromine and iodine.

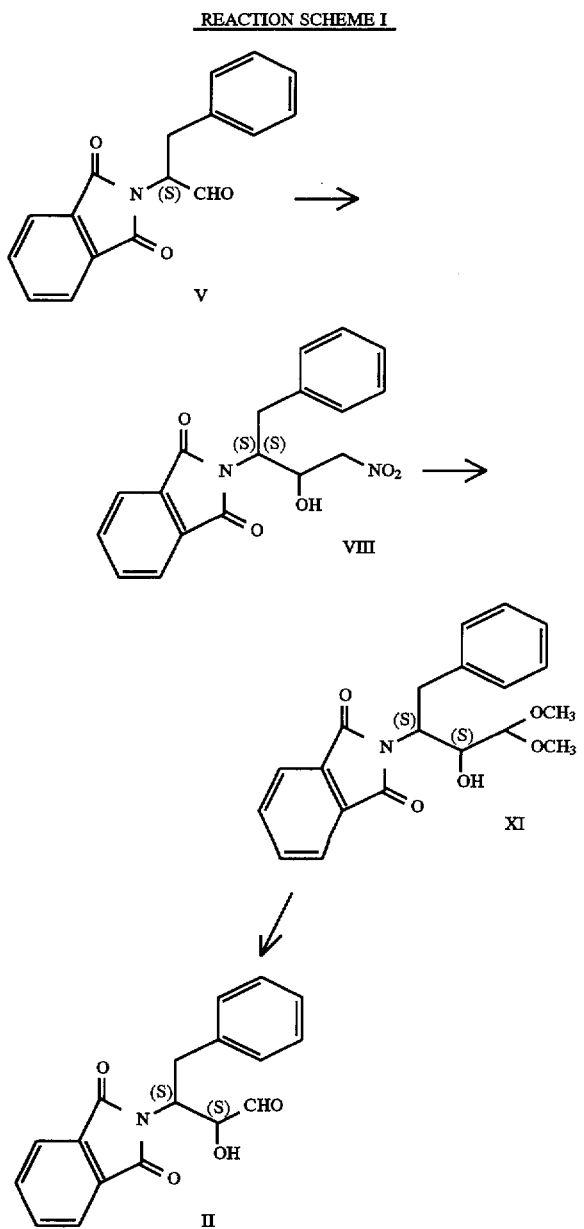

REACTION SCHEME I

The starting material, 3-Phenyl-2(S)-phthalimidopropan-1-al of formula V, is obtained by heating L-phenylalanine with phthalic anhydride in toluene, reacting the resulting N-protected L-phenylalanine with oxalyl chloride in toluene and catalytic amounts of dimethyl-formamide and catalytically (Pd/C) hydrogenating the resulting acid chloride corresponding to the desired aldehyde of formula V in the presence of 1,2-butylene oxide in toluene.

In the Reaction Scheme I, 3-phenyl-2(S)-phthalimidopropan-1-al of formula V is reacted with nitromethane in the presence of a base in a known manner. This reaction can be conveniently carried out in a solvent such as tetrahydrofuran and the like, while cooling, for example to −200° to +5° C., preferably to −15° to 0° C. Catalytic or stoichiometric amounts of a base such as potassium tert.butylate, Na methylate or aluminium oxide are conveniently used. The desired (1S,2R)-isomer of the resulting mixture of (1S,2S) and (1S,2R) isomers of 2-(1-benzyl-2-hydroxy-3-nitropropyl)-2,3-dihydro-1H-isoindole-1,3-dione of formula VIII can be enriched by crystallization, for example from tert.butyl methyl ether, or isolated in pure form by chromatography, for example on silica gel with hexane/ethyl acetate.

The thus-obtained (1 S,2R)-2-(1-benzyl-2-hydroxy-3-nitropropyl)-2,3-dihydro-1H-isoindole-1,3-dione of formula VIII is converted in the next step into (1S,2S)-2-(1-benzyl-2-hydroxy-3,3-dimethoxypropyl)-2,3-dihydro-1H-isoindole-1,3-dione of formula XI, likewise in a known manner, namely, by reaction with an alkali metal alcoholate such as sodium methylate and an acid such as sulfuric acid, hydrochloric acid or hydrobromic acid. This reaction is preferably carried out in a solvent such as methanol while cooling, for example to −50° to +10° C., preferably to −35° C. In the last step of this sequence the thus-obtained hydroxyacetal of formula XI can be converted by acid treatment into the aldehyde of formula II, likewise by known methods. The acid treatment is conveniently effected in an organic solvent which is inert under the reaction conditions, such as an ether, for example tetrahydrofuran or dioxane, and the like at room temperature. A mineral acid such as hydrochloric acid or sulfuric acid especially comes into consideration as the acid.

The 1,3,2-dioxathiolane derivative of formula IV can also be obtained starting from 3-phenyl-2(S)-phthaliminopropan-1-al of formula V according to the sequence in the Reaction Scheme II.

REACTION SCHEME II

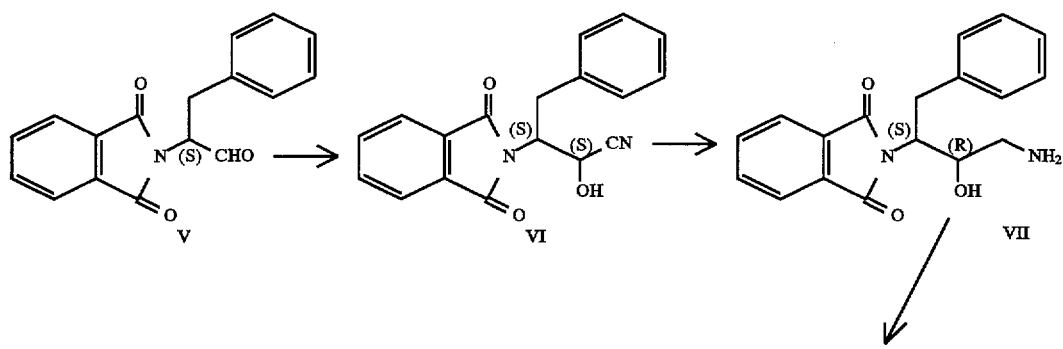

-continued
REACTION SCHEME II

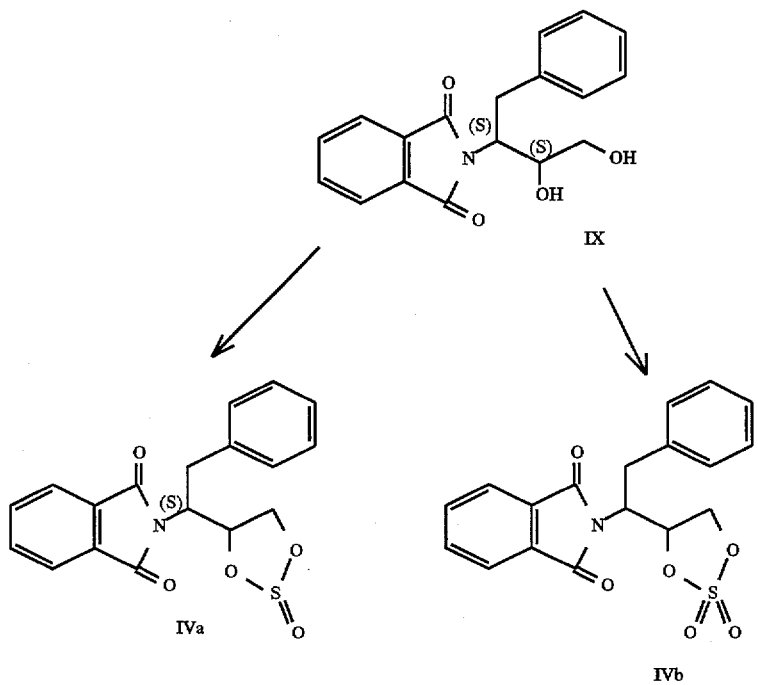

In the first step of Reaction Scheme II, the aldehyde of formula V is converted in a known manner into (2S,3S)-3-(1,3-dioxo-2,3-dihydro-1H-isoindol-2-yl)-2-hydroxy-4-phenylbutyronitrile of formula VI. For this purpose, a solution of the aldehyde of formula V, for example in toluene, is treated with aqueous sodium pyrosulfite and the resulting addition product of pyrosulfite and the aldehyde, optionally in a solvent such as water or optionally aqueous dichloromethane or toluene, is treated with sodium cyanide. In a variant, a mixture of the aldehyde of formula V and zinc-(II) bromide in a solvent such as methylene chloride is reacted at −70° to 0° C., for example −15° C., with trimethylsilyl cyanide and the resulting silyl ether of the cyanohydrin is cleaved by the addition of a solution of citric acid in ethanol.

In the next step, the cyanohydrin of formula VI obtained is converted into (1S,2R)-2-(3-amino-1-benzyl-2-hydroxypropyl)-2,3-dihydro-1H-isoindole-1,3-dione of formula VII, likewise in a known manner, namely, by hydrogenation in the presence of a catalyst such as platinum oxide, palladium or Raney-nickel, preferably platinum oxide, and reaction with an acid such as a mineral acid, sulfonic acid or alkanecarboxylic acid, preferably acetic acid, in a solvent such as an alcohol or an alkane-carboxylic acid, preferably acetic acid. The hydrogenation is effected at a pressure of about 100–5000 kPa, preferably about 100 kPa, and at a temperature between about −15° and 80° C., preferably at room temperature.

Subsequently, the aminoalcohol of formula VII is converted, likewise in a known manner, into the diol of formula IX, (1S,2S)-2-(1-benzyl-2,3-dihydroxypropyl)-2,3-dihydro-1H-isoindole-1,3-dione. This conversion via the diazonium salt is also effected according to known methods using sodium nitrite in the presence of an aqueous mineral acid or carboxylic acid, preferably in a 1:1 mixture of acetic acid and water, at a temperature between about 0° and 4° C, preferably at about 0° C., The aminoalcohol of formula VII need not be isolated prior to the conversion into the diol of formula IX; rather, the sequence VI→VII→IX is conveniently effected in one pot.

Alternatively, the hydrogenation of the cyanohydrin of formula VI can be carried out in the presence of at least 1 mol equivalent of acid and 1 mol equivalent of water. In this case a mixture of the aldehyde of formula II and the diol of formula IX is obtained directly, as shown in Reaction Scheme III, with the ratio depending on the reaction conditions which are used.

REACTION SCHEME III

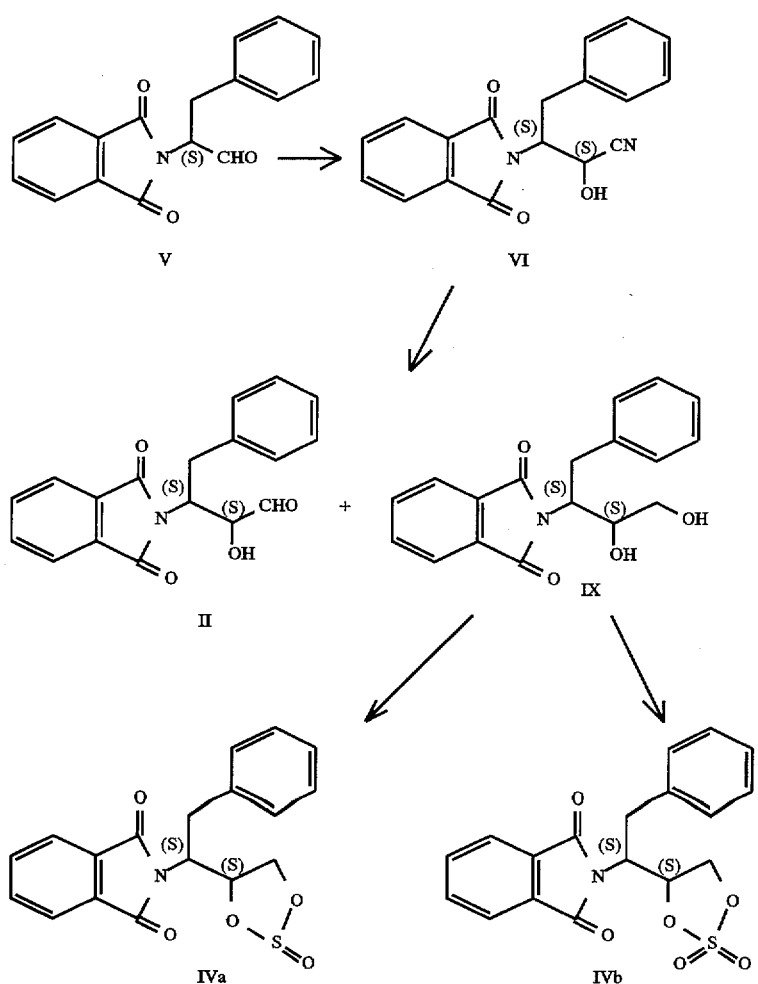

The procedure set forth in Reaction Scheme III can be effected according to known methods in the presence of a catalyst such as palladium, platinum oxide or Raney-nickel, preferably palladium-on-charcoal, and 1 mol equivalent of an inorganic or organic acid such as hydrochloric acid or acetic acid and the like or of an acidic ion exchanger such as Dowex 50 W×4,H⁺ and the like, and 1 mol equivalent of water in an organic solvent which is inert under the reaction conditions, such as an alcohol, for example isopropanol, and the like at a temperature between about −150° and 100° C., conveniently at room temperature, and a pressure of about 100–15000 kPa, preferably 100–1000 kPa.

As shown in Reaction Schemes II and III, the diol of formula IX can then be converted in a further step into a 1,3,2-dioxathiolane derivative of formula IV.

If the compound of formula IVa is desired, then the diol of formula IX is reacted with thionyl chloride in a known manner in the presence of an organic base, preferably an amine such as an alkylamine, for example, triethylamine or Hünig base, in an organic solvent which is inert under the reaction conditions, such as an ether, for example, diethyl ether, tetrahydrofuran or dioxane, and the like at a temperature between about −15° and 80° C., preferably at about 0° C. A 1:1 mixture of the two isomers 2-[(S)-1-[(2R,4S)- and [(2S,4S)-2-oxo-1,3,2-dioxathiolan-4-yl]-2-phenylethyl]-2, 3-dihydro-1H-isoindole-1,3-dione is thus formed.

If, on the other hand, the compound of formula IVb is desired, then the reaction is effected, likewise in a known manner, with thionyl chloride without the addition of an organic base at a temperature between about room temperature and 80° C., preferably at about 80° C., in an organic solvent which is inert under the reaction conditions, such as a chlorinated hydrocarbon, for example carbon tetrachloride, and the like. In a second reaction step the crude product is reacted with an oxidation agent in a solvent mixture such as for example carbon tetrachloride/ acetonitrile/water, and the like. This reaction step is also effected according to known methods. An oxidation agent which is suitable for the purpose of the invention is for example a stoichiometric amount of sodium periodate in the presence of a catalytic amount of ruthenium chloride at a temperature between about 0° and 50° C., preferably at room temperature.

The invention also relates to a process for the preparation of the compound of formula I as shown in Reaction Scheme IV.

REACTION SCHEME IV

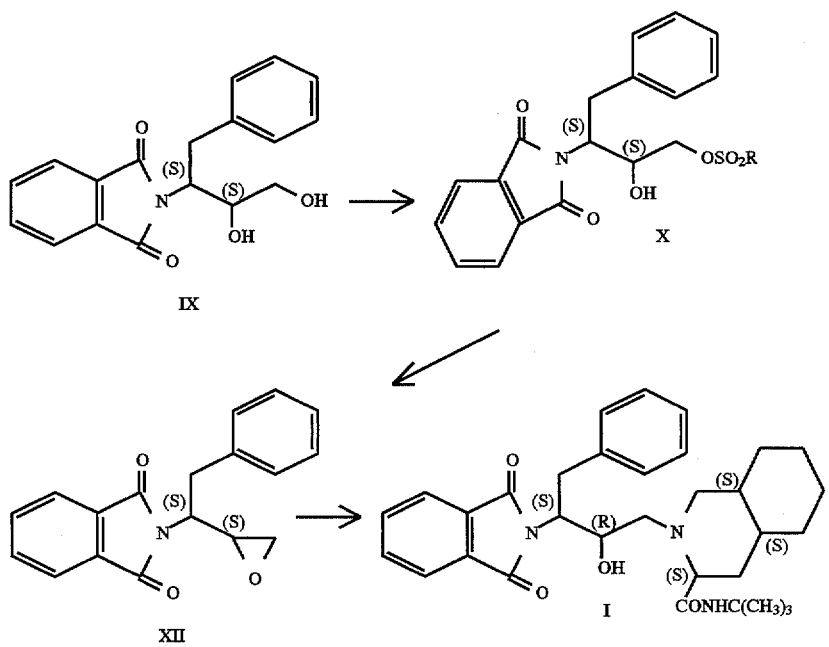

In Reaction Scheme IV, the diol of formula IX is converted in a known manner with a sulfonyl chloride of the formula

wherein R is as described above, in the presence of an organic base such as pyridine, piperidine, an alkylamine, for example triethylamine, and the like in an organic solvent which is inert under the reaction conditions, such as an aromatic hydrocarbon, for example toluene or xylene, an alkanecarboxylic acid ester, for example ethyl acetate, and the like into a compound of formula X, the resulting compound of formula X is then converted, likewise according to known methods, in the presence of a strong base such as an alkali metal hydride, for example sodium hydride, or an alkali metal alkoxide, for example potassium tert.-butylate, and the like in an organic solvent which is inert under the reaction conditions, such as dimethylformamide or an ether, for example diethyl ether, tetrahydrofuran or dioxan, and the like at a temperature between about −15° to 50° C., preferably at about −15° C., into the epoxide 2(S)-[2-phenyl-1(S)-phthalimidoethyl]oxirane of the formula XII.

The epoxide of formula XII as well as its conversion into the compound of formula I is specifically known and is described in Example 1 of European Patent Publication 0,432,694.

The compounds of formulas II, IV, VII, VIII, IX, X and XI also form part of the invention.

The Examples which follow further illustrate the invention. All temperatures are given in degrees Celsius.

EXAMPLE 1

A) A suspension of 82.6 g of L-phenylalanine and 74.1 g of phthalic anhydride in 600 ml of toluene is heated to reflux under argon for 8 hours. The resulting suspension is cooled to room temperature treated with 0.5 ml of dimethylformamide, followed by 66.64 g of oxalyl chloride. After stirring for 2 hours argon is bubbled into the suspension.

B) The solution containing the 3-phenyl-2(S)-phthalimidopropionyl chloride is diluted with 500 ml of toluene and treated with 72.11 g of 1,2-butylene oxide. 23.5 g of palladium-on-charcoal (5%) and 100 ml of toluene are added to the solution. The suspension is hydrogenated for 17 hours while stirring and then filtered, and the residue is washed with 200 ml of toluene. The filtrate and washings are combined and treated while stirring with a solution of 0.5 mol of sodium pyrosulfite in water. The phases are separated after 4.5 hours. The aqueous phase is washed with toluene. The toluene phases are washed with water. The combined aqueous phases are treated with toluene and 3N sulphuric acid and stirred at 60°. Thereafter, the phases are separated and the aqueous phase is extracted with toluene. The toluene phases are washed with water, combined, dried and evaporated. 3-Phenyl-2(S)-phthalimidopropan-1-al is obtained as a white solid, melting point 115°–117°, $[a]_D^{20}$ −200° (1% in ethyl acetate).

C) A solution of 20.0 g of 3-phenyl-2(S)-phthalimidopropan-1-al and 5.8 g of nitromethane in 120 ml of tetrahydrofuran is treated while stirring at −15° with a solution of 1.5 g of potassium tert.butylate in 15 ml of tetrahydrofuran and the mixture is stirred at −15° for 1 hour and at 0° for 1 hour. The pH value of the yellow solution is adjusted to 4 with 6 ml of 3N hydrochloric acid and the solution is washed with 50 ml of saturated sodium chloride solution. The organic phase is dried and filtered, and the filtrate is concentrated to give 25 g (100%) of a 64:36 mixture of (1S,2R)-2-(1-benzyl-2-hydroxy-3-nitropropyl)-2,3-dihydro-1H-isoindole-1,3-dione and (1S,2S)-2-(1-benzyl-2-hydroxy-3-nitropropyl)-2,3-dihydro-1H-isoindole-1,3-dione, IR (KBr): 3550 m (OH), 1766 s and 1703 s (C=O of imide), 1556 s and 1388 s ($NO_2$). The (1S,2S) isomer can be separated from the crude product by crystallization from tert.butyl methyl ether. The two isomers can also be separated on silica gel with hexane/ethyl acetate (3:1).

D) A suspension of 1.02 g of an 87:13 mixture of the (1S,2R) and (1S,2S) isomers of 2-(1-benzyl-2-hydroxy-3- nitropropyl)-2,3-dihydro-1H-isoindole-1,3-dione in 2 ml of methanol is treated at 0° with 5.7 ml of a 7% solution of sodium methylate in methanol and the resulting yellow solution is added dropwise over a period of 20 minutes to a solution, cooled to −350°, of 7.2 ml of sulfuric acid in 27.6 ml of methanol. The reaction mixture is subsequently added to a stirred mixture of 150 ml of methylene chloride and 70 ml of ice-water and the aqueous phase is extracted with methylene chloride. The combined methylene chloride phases were dried, filtered and concentrated, and the residue was purified on silica gel with hexane/ethyl acetate (3:1). After evaporation and drying there is obtained 0.52 g (49%) of pure (1S,2S)-2-(1-benzyl-2-hydroxy-3,3-dimethoxypropyl)-2,3-dihydro-1H-isoindole-1,3-dione as a colourless oil, IR (film): 3465 m (OH), 1772 s and 1708 s (C=O of imide), 1071 s (C—O—C).

E) A solution of 107 mg of (1S,2S)-2-(1-benzyl-2-hydroxy-3,3-dimethoxypropyl)-2,3-dihydro-1H-isoindole-1,3-dione in 0.5ml of tetrahydrofuran and 0.5 ml of 3N hydrochloric acid is stirred at room temperature for 23 hours and thereafter concentrated completely. The residue is purified on silica gel with hexane/ethyl acetate (2:1). After evaporation and drying there are obtained 63 mg (68%) of 2S,3S)-3-(1,3-dioxo-2,3-dihydro-1H-isoindol-2-yl)-2-hydroxy-4-phenyl-butyraldehyde as a colorless foam, MS:309.

F1) 309 mg of (2S,3S)-3-(1,3-dioxo-2,3-dihydro-1H-isoindol-2-yl)-2-hydroxy-4-phenylbutyraldehyde and 238 mg of N-tert.butyl-decahydro-(4aS,8aS)-isoquinoline-3(S)-carboxamide are dissolved in 5 ml of acetic acid and treated portionwise with 120 mg of sodium cyanoborohydride. After completion of the reaction the mixture is concentrated to dryness, treated with 10 ml of water and extracted with methylene chloride. The extracts are dried and filtered, the filtrate is concentrated and the residue is purified on silica gel with methylene chloride/methanol (95:5). N-tert.Butyl-decahydro-2-[2(R)-hydroxy-4-phenyl-3(S)-phthalimidobutyl]-(4aS,8aS)-isoquinoline-3(S)-carboxamide is obtained.

F2) In a variant to paragraph F1), a solution of (2S,3S)-3-(1,3-dioxo-2,3-dihydro-1H-isoindol-2-yl)-2-hydroxy-4-phenylbutyraldehyde in a mixture of 5 ml of methanol and 35 mg of hydrogen chloride is used.

F3) In a further variant to paragraph F1), 309 mg of (2S,3S)-3-(1,3-dioxo-2,3-dihydro-1H-isoindol-2-yl)-2-hydroxy-4-phenylbutyraldehyde and 238 mg of N-tert.butyl-decahydro-(4aS,8aS)-isoquinoline-3(S)-carboxamide are dissolved in 5 ml of formic acid and heated to 100° C. until the educt has reacted completely. The working-up is effected as described under paragraph F1).

EXAMPLE 2

A1) A suspension of 5 g of 3-phenyl-2(S)-phthalimidopropan-1-al and 4.43 g of zinc bromide in 50 ml of methylene chloride is treated while stirring at −15° with a solution of 1.95 g of trimethylsilyl cyanide in 5 ml of methylene chloride and the mixture is stirred at −15° for 5 hours. The silyl ether formed is cleaved by the addition of a solution of 5 g of citric acid in 50 ml of ethanol at −10°. The mixture is concentrated and the residue is treated with water and extracted with methylene chloride. The organic extracts are dried and filtered, and the filtrate is concentrated. The residue contains 5.45 g (99%) of crude 3-(1,3-dioxo-2,3-dihydro-1H-isoindol-2-yl)-2-hydroxy-4-phenylbutyronitrile as a 74:26 mixture of the (2S,3S) and (2R,3S) isomers, IR (KBr): 3437 m (OH), 2250 w (C≡N), 1775 m and 1713 s (C=O of imide).

A2) A solution of 95.05 g of sodium pyrosulphite in 1 l of water is added at room temperature while stirring to the solution containing 3-phenyl-2(S)-phthalimidopropan-1-al. After stirring for 4.5 hours the aqueous layer containing the addition product of bisulphite and the above aldehyde is washed with toluene. The toluene layers are extracted with water. 1200 ml of methylene chloride are added to the aqueous layers and the mixture is treated while stirring at room temperature with a solution of 41.66 g of sodium cyanide in 330 ml of water. After stirring for 1.2 hours water is added. The separated aqueous layer is extracted with methylene chloride. The organic layers are dried and filtered, and the residue is washed with methylene chloride. The filtrates are evaporated and the residue is dissolved in 200 ml of methylene chloride. The solution is treated dropwise while stirring at 30° with 600 ml of hexane and then at 0° with a further 600 ml of hexane. The suspension is filtered and the residue is washed with hexane and then dried. There were obtained 114.02 g (74%) of a 74.7:23.5:1.4:0.4 mixture of the (2S,3S):(2R,3S):(2R,3R):(2S,3R) isomers of 3-(1,3-dioxo-2,3-dihydro-1H-isoindol-2-yl)-2-hydroxy-4-phenylbutyronitrile, m.p. 127.2°–130.5°, $[a]_D^{20}$: −146.6° (1% in methylene chloride).

A3) A solution of 47.5 g of sodium pyrosulfite in 500 ml of water is added at room temperature while stirring to the solution containing 3-phenyl-2(S)-phthalimidopropan-1-al. After stirring for 7.5 hours the aqueous layer containing the addition product of pyrosulfite and the above aldehyde is washed with toluene. The toluene layers are extracted with water. A solution of 24.2 g of sodium cyanide in 200 ml of water is added to the aqueous layers while stirring at room temperature. After stirring for 1 hour the suspension is filtered and the residue is washed neutral with water. After drying there are obtained 112.03 g (73%) of a 67.2;32.8 mixture of the (2S,3S):(2R,3S) isomers of 3-(1,3-dioxo-2,3-dihydro-1H-isoindol-2-yl)-2-hydroxy-4-phenylbutyronitrile, m.p. 131°–133°, $[a]_D^{20}$: −150.2° (1% in methylene chloride).

B) A suspension of 20.0 g of a 75:25 mixture of the (2S,3S) and (2R,3S) isomers of 3-(1,3-dioxo-2,3-dihydro-1H-isoindol-2-yl)-2-hydroxy-4-phenylbutyronitrile and 2 g of platinum oxide in 200 ml of acetic acid is hydrogenated for 2 hours at room temperature and atmospheric pressure, with 4000 ml of hydrogen being taken up. The suspension is treated with 3 g of active charcoal, stirred for 1 hour and filtered. The filtrate, which contains (1S,2R)-2-(3-amino-1-benzyl-2-hydroxy-propyl)-2,3-dihydro-1H-isoindole-1,3-dione acetate, is diluted with 200 ml of water, cooled to 0°, treated with a solution of 4.50 g of sodium nitrite in 6 ml of water, stirred at 0° for 3 hours, again treated with a solution of 4.50 g of sodium nitrite in 6 ml of water and finally stirred at 0° for a further 2 hours. Thereafter, the reaction mixture is extracted with methylene chloride. The extracts are washed with water, dried and filtered, and the filtrate is concentrated. The residue is purified on silica gel with methylene chloride/isopropanol (100:1). After evaporation and drying there are obtained 6.25 g (31%) of an 83:17 mixture of the (1S,2S) and (1S,2R) isomers of 2-(1-benzyl-2,3-dihydroxypropyl)-2,3-dihydro-1H-isoindole-1,3-dione, IR: 3460 (OH), 1771 m and 1701 s (C=O of imide).

C) A solution of 0.51 g of an 83:17 mixture of the (1S,2S) and (1S,2R) isomers of 2-(1-benzyl-2,3-dihydroxypropyl)-2,3-dihydro-1H-isoindole-1,3-dione and 0.28 ml of triethylamine in 5 ml of tetrahydrofuran is cooled to 0°, treated with 0.15 ml of thionyl chloride and stirred at 0° for 1 hour. The reaction mixture is treated with 4 ml of semi-saturated sodium chloride solution and 1 ml of 1N sulfuric acid and extracted with ethyl acetate. The extracts are dried and filtered, and the filtrate is evaporated to give 0.60 g (100%)

of 83 parts of a 1:1 mixture of the (2R,4S) and (2S,4S) isomers of 2-[(S)-1-[2-oxo-1,3,2-dioxathiolan-4-yl]-2-phenylethyl]-2,3-dihydro-1H-isoindole-1,3-dione as well as 17 parts of a 1:1 mixture of the (2R,4R) and (2S,4R) isomers of 2-[(S)-1-[2-oxo-1,3,2-dioxathiolan-4-yl]-2-phenylethyl]-2,3-dihydro-1H-isoindole-1,3-dione, IR (KBr): 1777 m and 1713 s (C=O of imide), 1384 s and 1212 s (SO₃).

D) A suspension of 0.35 g of the above 83:17 mixture of the two 1:1 mixtures of the (2R,4S) and (2S,4S) and respectively (2R,4R) and (2S,4R) isomers of 2-[(S)-1-[2-oxo-1,3,2-dioxathiolan-4-yl]-2-phenylethyl]-2,3-dihydro-1H-isoindol-1,3-dione, 0.24 g of N-tert.butyl-decahydro-(4aS,8aS)-isoquinoline-3(S)-carboxamide and 0.21 g of sodium carbonate in 3.5 ml of isobutyl methyl ketone is heated to reflux for 24 hours, thereafter cooled and filtered. The filtrate is purified on silica gel with hexane/ethyl acetate (4:1). After evaporation and drying there is obtained 0.34 g (65%) of pure N-tert.butyl-decahydro-2-[2(R)-hydroxy-4-phenyl-3(S)-phthalimidobutyl]-(4aS,8aS)-isoquinoline-3(S)-carboxamide, IR (KBr): 3388 m (OH), 1771 m and 1708 s (C=O of imide).

EXAMPLE 3

A) A mixture of 3.1 g of an 83:17 mixture of (1S,2S) and (1S,2R) isomers of 2-(1-benzyl-2,3-dihydroxypropyl)-2,3-dihydro-1H-isoindole-1,3-dione and 10 ml of carbon tetrachloride is treated with 0.9 ml of thionyl chloride and heated to reflux for 0.5 hour. The mixture is diluted at 0° with 10 ml of acetonitrile and treated in succession with 2 mg of ruthenium trichloride trihydrate, 3.2 g of sodium periodate and 15 ml of water and stirred at room temperature for 1 hour. The mixture is extracted with ether and the extracts are washed with dilute sodium bicarbonate solution and water. Drying, filtration and concentration of the filtrate yields an 83:17 mixture of 2-[(S)-1-[(4S) and (4R)-2-dioxo-1,3,2-dioxathiolan-4-yl]-2-phenylethyl]-2,3-dihydro-1H-isoindole-1,3-dione.

B) A solution of 0.37 g of an 83:17 mixture of 2-[(S)-1-[(4S)- and (4R)-2-dioxo-1,3,2-dioxathiolan-4-yl]-2-phenylethyl]-2,3-dihydro-1H-isoindole-1,3-dione and 0.24 g of N-tert.butyl-decahydro-(4aS,8aS)-isoquinoline-3(S)-carboxamide in 2 ml of tetrahydrofuran is stirred until the reaction has finished, subsequently treated with 5 ml of 20% sulfuric acid and 5 ml of ether, stirred for 10 hours and extracted with ether. The extracts are washed with water, dried and filtered, and the filtrate is evaporated to give N-tert.butyl-decahydro-2-[2(R)-hydroxy-4-phenyl-3(S)-phthalimidobutyl]-(4aS,8aS)-isoquinoline-3(S)-carboxamide, IR (KBr): 3388 m (OH), 1771 m and 1708 s (C=O of imide).

EXAMPLE 4

A) A solution of 0.51 g of an 83:17 mixture of the (1S,2S) and (1S,2R) isomers of 2-(1-benzyl-2,3-dihydroxypropyl)-2,3-dihydro-1H-isoindole-1,3-dione, 0.4 ml of pyridine and 1 ml of ethyl acetate is treated with 0.15 ml of methanesulfonyl chloride and the mixture is stirred at room temperature for 4 hours. The mixture is diluted with ethyl acetate and washed with 2% hydrochloric acid, and the extracts are dried and filtered. The filtrate is evaporated and the residue is purified on silica gel with methylene chloride/isopropanol (100:1). After evaporation and drying there is obtained 0.28 g (43%) of pure methanesulfonic acid (2S,3S)-3-(1,3-dioxo-2,3-dihydro-1H-isoindol-2-yl)-2-hydroxy-4-phenylbutyl ester, NMR (CDCl₃): 7.7 (m,4H); 7.1 (m,5H); 4.6 (m,2H); 4.3 (m,2H); 3.55 (d,J=7,1H); 3.3 (m,2H); 3.1 (s,3H).

B) A solution of 0.26 g of methanesulfonic acid (2S,3S)-3-(1,3-dioxo-2,3-dihydro-1H-isoindol-2-yl)-2-hydroxy-4-phenylbutyl ester in 1.6 ml of tetrahydrofuran is treated at −15° with a solution of 0.090 g of potassium tert.butylate in 0.5 ml of tetrahydrofuran and the mixture is stirred for 0.5 hours. The mixture is treated with 2.2 ml of semi-saturated sodium chloride solution and the pH value is adjusted to 6 with 0.1 ml of 1N sulphuric acid. Thereafter, the mixture is extracted with ethyl acetate. The extracts are dried and filtered, and the filtrate is evaporated to give 0.12 g (60%) of 2(S)-[2-phenyl-1(S)-phthalimidoethyl]oxirane, IR (KBr): 1773 m and 1709 s (C=O of imide).

EXAMPLE 5

A suspension of 10.0 g of a 75:25 mixture of the (2S,3S) and (2R,3S) isomers of 3-(1,3-dioxo-2,3-dihydro-1H-isoindol-2-yl)-2-hydroxy-4-phenylbutyronitrile, 2.7 ml of 37% hydrochloric acid, 50 ml of isopropanol and 50 ml of water is treated with 1 g of palladium-on-charcoal (10%) and hydrogenated at 100 kPa for 5 hours. The reaction mixture is filtered and the concentrated filtrate is purified by chromatography to give a mixture of (2S,3S)-3-(1,3-dioxo-2,3-dihydro-1H-isoindol-2-yl)-2-hydroxy-4-phenylbutyraldehyde and (1S,2S)-2-(1-benzyl-2,3-dihydroxypropyl)-2,3-dihydro-1H-isoindole-1,3-dione. IR (KBr) of (1S,2S)-(2S,3S)-3-(1,3-dioxo-2,3-dihydro-1H-isoindol-2-yl)-2-hydroxy-4-phenylbutyraldehyde: 3451 m (OH), 1774 m and 1711 s (C=O of the imide); IR of (1S,2S)-2-(1-benzyl-2,3-dihydroxypropyl)-2,3-dihydro-1H-isoindole-1,3-dione: 3460 m (OH).

In place of 2.7 ml of 37% hydrochloric acid there can also be used 30 ml of moist ion exchanger (Dowex 50 W×4,H⁺), with (2S,3S)-3-(1,3-dioxo-2,3-dihydro-1H-isoindol-2-yl)-2-hydroxy-4-phenylbutyraldehyde being preferentially obtained.

I claim:

1. A process for the preparation of a compound of the formula

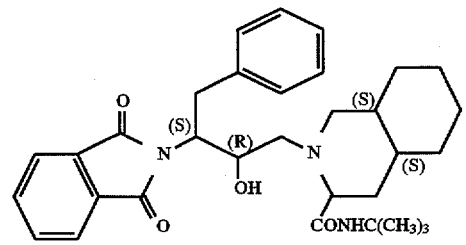

I which process comprises reacting a 1,3,2-dioxathiolane derivative of the formula

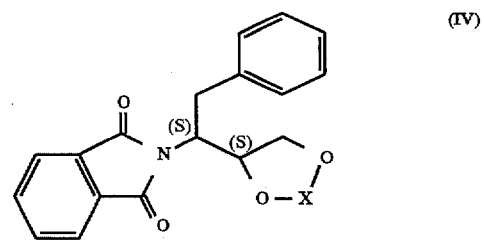

(IV)

when X is SO or SO₂, with a compound of the formula

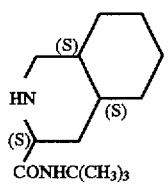

III

2. A process for the preparation of a compound of the formula

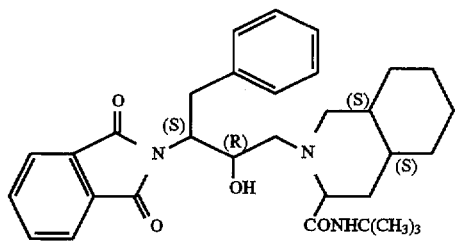

I which process comprises:

(a) reacting a compound of the formula

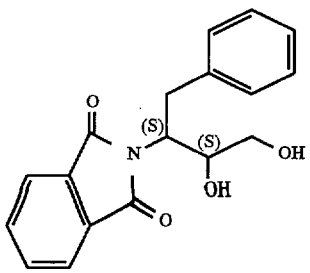

IX with a sulfonyl chloride of the formula

RSO₂Cl wherein R is unsubstituted lower alkyl, unsubstituted phenyl, lower alkyl substituted by one or two halogen atoms, or phenyl substituted by one or two halogen atoms;

(b) reacting a resulting compound of the formula

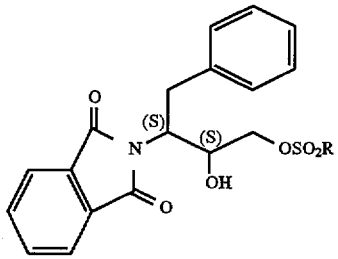

X wherein R is as described above with a strong base; and (c) reacting a resulting compound of the formula

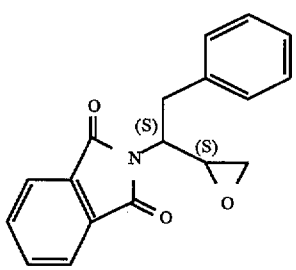

XII with a compound of the formula

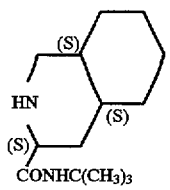

III

* * * * *